United States Patent
Paulsen

(10) Patent No.: US 7,115,719 B2
(45) Date of Patent: Oct. 3, 2006

(54) FORMULATIONS AND METHODS FOR DENATURING PROTEINS

(75) Inventor: Kim E. Paulsen, Brooklyn Park, MN (US)

(73) Assignee: Gentra Systems, Inc., Minneapolis, MN (US)

( * ) Notice: Subject to any disclaimer, the term of this patent is extended or adjusted under 35 U.S.C. 154(b) by 0 days.

(21) Appl. No.: 11/012,527

(22) Filed: Dec. 15, 2004

(65) Prior Publication Data

US 2005/0171333 A1 Aug. 4, 2005

Related U.S. Application Data

(60) Provisional application No. 60/530,392, filed on Dec. 16, 2003.

(51) Int. Cl.
*C07K 1/14* (2006.01)

(52) U.S. Cl. .................. 530/427; 530/412; 530/418; 435/91.1; 435/814; 436/178

(58) Field of Classification Search ................ 530/427, 530/412, 418; 435/91.1, 814; 436/178
See application file for complete search history.

(56) References Cited

U.S. PATENT DOCUMENTS

| | | | |
|---|---|---|---|
| 4,133,753 A | 1/1979 | Takeuchi et al. | |
| 4,843,155 A | 6/1989 | Chomczynski | |
| 5,010,183 A | 4/1991 | Macfarlane | |
| 5,234,809 A | 8/1993 | Boom et al. | |
| 5,346,994 A | 9/1994 | Chomczynski | |
| 5,405,951 A | 4/1995 | Woodard | |
| 5,422,241 A | 6/1995 | Goldrick et al. | |
| 5,480,973 A | 1/1996 | Goodlad et al. | |
| 5,599,667 A | 2/1997 | Arnold, Jr. et al. | |
| 5,652,141 A | 7/1997 | Henco et al. | |
| 5,677,124 A | 10/1997 | DuBois et al. | |
| 5,705,382 A | 1/1998 | Endo et al. | |
| 5,728,822 A | 3/1998 | Macfarlane | |
| 5,919,625 A | 7/1999 | Dubois et al. | |
| 5,939,262 A | 8/1999 | Pasloske et al. | |
| 5,945,515 A | 8/1999 | Chomczynski | |
| 5,973,137 A | 10/1999 | Heath | |
| 5,985,572 A | 11/1999 | Macfarlane | |
| 5,990,302 A | 11/1999 | Kuroita et al. | |
| 6,020,186 A | 2/2000 | Henco et al. | |
| 6,123,934 A | 9/2000 | Koyama et al. | |
| 6,204,375 B1 | 3/2001 | Lader | |
| 6,214,982 B1 | 4/2001 | Pasloske et al. | |
| 6,383,393 B1 | 5/2002 | Colpan et al. | |
| 6,399,307 B1 | 6/2002 | Pasloske et al. | |
| 6,528,641 B1 | 3/2003 | Lader | |
| 6,777,210 B1 | 8/2004 | Pasloske et al. | |
| 6,825,340 B1 | 11/2004 | Pasloske et al. | |
| 2002/0026046 A1 | 2/2002 | Pasloske et al. | |
| 2002/0044919 A1 | 4/2002 | Yu | |
| 2002/0192689 A1 | 12/2002 | Pasloske et al. | |
| 2003/0073830 A1 | 4/2003 | Heath et al. | |
| 2003/0114651 A1 | 6/2003 | Lader | |
| 2004/0019196 A1 | 1/2004 | Bair et al. | |
| 2005/0032105 A1 | 2/2005 | Bair et al. | |
| 2005/0191760 A1 | 9/2005 | Heath et al. | |

FOREIGN PATENT DOCUMENTS

| | | |
|---|---|---|
| WO | WO 92/07863 | 5/1992 |
| WO | WO 95/01359 | 1/1995 |
| WO | WO 95/02049 | 1/1995 |
| WO | WO 99/13976 | 3/1999 |
| WO | WO 00/17320 | 3/2000 |
| WO | WO 03/033739 | 4/2003 |
| WO | WO 2004/094635 | 11/2004 |

OTHER PUBLICATIONS

"Answers to Frequently Asked Questions about RT-PCR", *Focus*, 22(1), 13 (2000).
International Search Report for International Application No. PCT/US04/42044, mailed Jun. 07, 2005.
Chomczynski et al., "Single-Step Method of RNA Isolation by Acid Guanidinium Thiocyanate-Phenol-Chloroform Extraction", *Analytical Biochemistry*, 162, 156-159 (1987).
Collins, "Sticky Ions in Biological Systems", *PNAS*, 92, 5553-5557 (1995).
Zale et al., "Why Does Ribonuclease Irreversibly Inactivate at High Temperatures?", *Biochemistry*, 25, 5432-5444 (1986).

*Primary Examiner*—David Lukton
(74) *Attorney, Agent, or Firm*—Viksnins Harris & Padys PLLP

(57) ABSTRACT

Reagents, methods and kits for denaturation of protein are provided.

23 Claims, No Drawings

FORMULATIONS AND METHODS FOR DENATURING PROTEINS

This application claims priority to provisional application 60/530,392, filed Dec. 16, 2003.

BACKGROUND OF THE INVENTION

Nucleic acids such as deoxyribonucleic acid (DNA) and ribonucleic acid (RNA) are used extensively in the field of molecular biology for research and clinical analyses. RNA may be found in nature in various forms, including messenger RNA (mRNA), transfer RNA (tRNA), ribosomal RNA (rRNA), and viral RNA. Each of these types of RNA has distinct properties related to their specific functions. Analysis of RNA expression levels and patterns provides important information in fields such as developmental genetics, drug discovery and clinical diagnostics. For example, RNA analysis provides important diagnostic information about both normal and aberrant functioning of genes. Furthermore, gross DNA rearrangements associated with common leukemias are detected by isolation and identification of abnormal, hybrid RNAs.

Common methods for analyzing RNA include northern blotting, ribonuclease protection assays (RPAs), reverse transcriptase-polymerase chain reaction (RT-PCR), cDNA preparation for cloning, in vitro translation and microarray analyses. To obtain valid and consistent results from these analyses, it is important that the RNA be purified from other components common to biological materials such as proteins, carbohydrates, lipids and DNA.

SUMMARY OF THE INVENTION

It should be noted that the indefinite articles "a" and "an" and the definite article "the" are used in the present application, as is common in patent applications, to mean one or more unless the context clearly dictates otherwise. Further, the term "or" is used in the present application, as is common in patent applications, to mean the disjunctive "or" or the conjunctive "and."

The present invention provides a formulation for denaturing proteins that contains a lithium salt at a concentration of about 2.5–4.0 M, an alcohol at a concentration of about 25–40% v/v, and a citrate at a concentration of about 25–100 mM. This formulation lacks EDTA, and lacks a chaotropic substance (e.g., guanidinium salt, urea, ammonium, cesium, rubidium, potassium, or iodide salt). In certain embodiments, the lithium salt is lithium chloride or lithium bromide. In one embodiment, the lithium salt is at a concentration of about 3.5 M. In one embodiment, the alcohol is ethanol or methanol. In one embodiment the alcohol is at a concentration of about 30% alcohol. In one embodiment the citrate is trisodium citrate. In one embodiment, the citrate is at a concentration of about 50 mM. In certain embodiments, the formulation has a pH between about 6 and about 8 (such as between about 7.0 and about 7.5).

The present invention also provides a method for denaturing protein (such as an enzyme) from a solid support, by contacting the solid support with the formulation described above, such that the protein present on the solid support is denatured. In one embodiment the enzyme to be denatured is a DNase, for instance DNase I. Examples of solid supports are components of silica, cellulose, cellulose acetate, nitrocellulose, nylon, polyester, polyethersulfone, polyolefin, or polyvinylidene fluoride, or combinations thereof In certain embodiments, the solid support is contained in a vessel, wherein the vessel is a centrifuge tube, spin tube, syringes, cartridge, chamber, multiple-well plate, or test tube, or combinations thereof.

The present method provides a method for purifying substantially pure and undegraded RNA from biological material comprising RNA. In this method, a solid support is contacted with the formulation described above, such that protein present on the solid support is denatured; the solid support is also contacted with a sample comprising RNA such that the RNA binds to the solid support; and the solid support is washed with a series of wash solutions to remove biological materials other than bound RNA, wherein the series of wash solutions comprises a first wash containing alcohol and an RNA-complexing salt at a concentration of 1 M and a second wash containing an alcohol, buffer and an optional chelator; and the bound RNA is preferentially eluted from the solid support with an RNA elution solution in order to obtain substantially pure RNA. The RNA-complexing salt used in the method of the present invention may be an alkali-metal salt, such as a lithium salt. Examples of appropriate lithium salts include lithium chloride or lithium bromide. The RNA-complexing salt may be present at a concentration greater than about 4 M. In one embodiment, the alkali metal salt may be present at a concentration of between 4–10 M.

In certain embodiments, the solid support is contained in a vessel, wherein the vessel is a centrifuge tube, spin tube, syringe, cartridge, chamber, multiple-well plate, test tube, or combination thereof.

The biological material that is the source of RNA used in the method of the present invention may be a crude sample or a partially purified mixture of nucleic acids. Examples of biological materials include a sample of eukaryotic cells, prokaryotic cells, microbial cells, bacterial cells, plant cells, mycoplasma, protozoa, bacteria, fungi, virus, yeast, or rickettsia, or homogenates thereof. Additional examples of biological materials include whole blood, bone marrow, blood spot, blood serum, blood plasma, buffy coat preparation, saliva, cerebrospinal fluid, or solid animal tissue. Further examples of biological materials include feces, urine, tears, or sweat. The biological material may also be an environmental sample taken from air, water, sediment or soil.

The solid support used in the methods of the present invention include components of silica, cellulose, cellulose acetate, nitrocellulose, nylon, polyester, polyethersulfone, polyolefin, or polyvinylidene fluoride, or combinations thereof. The solid support may be contained in a vessel, wherein the vessel is a centrifuge tube, spin tube, syringes, cartridge, chamber, multiple-well plate, or test tube, or combinations thereof.

The substantially pure and undegraded RNA subjected to the methods of the present invention include total RNA (i.e., an mixture of RNA found in a biological material such as all the types of RNA found in a cell), messenger RNA, transfer RNA, ribosomal RNA or viral RNA, or combinations thereof.

DETAILED DESCRIPTION OF THE INVENTION

RNA purification methods fall into two general categories, liquid phase and solid phase purification. In liquid phase purification, the RNA remains in the liquid phase, while impurities are removed by processes such as precipitation and/or centrifugation. In solid phase purification, the RNA is bound to a solid support while impurities such as DNA, proteins, and phospholipids are selectively eluted.

Both purification strategies utilize conventional methods, which require numerous steps and, often, hazardous reagents. When the starting biological material comprises cells, both methods require a cell or viral co-rupture or lysis step that results in a mixed RNA with contaminants such as DNA, lipids, carbohydrates, proteins, etc. Such mixtures also contain nucleases that easily degrade RNA and must be removed and/or inactivated.

Traditionally, liquid phase RNA isolation methods have used liquid-liquid extraction (i.e., phenol-chloroform) and alcohol precipitation. Perhaps the most commonly used liquid-liquid extraction method is the "acid-guanidinium-phenol" method of Chomczynski and Sacchi (Chomczynski P, Sacchi N., *Single-step method of RNA isolation by acid guanidinium thiocyanate-phenol-chloroform extraction*, Anal Biochem 162: 156–9 [1987]; U.S. Pat. Nos. 5,945,515, 5,346,994, and 4,843,155). This method comprises: (1) extracting the sample with a guanidinium isothiocyanate (GITC) solution to which an acidic medium, phenol, and chloroform are added consecutively; (2) centrifuging the mixture to separate the phases such that the proteins denatured by the phenol may be removed from the nucleic acids that are found in an intermediate layer; (3) adding an alcohol so as to precipitate and thereby concentrate the RNA; and (4) washing and re-hydrating the purified RNA. Although this method ensures the purification of RNA, it utilizes hazardous reagents such as chloroform and phenol. Precipitation of nucleic acids by cationic detergents is another example of liquid phase technology (U.S. Pat. Nos. 5,985,572; 5,728,822 and 5,010,183 (MacFarlane)). For example, U.S. Pat. No. 5,985,572 discloses a novel method for isolating RNA from biological samples using selected quaternary amine surfactants. A non-hazardous liquid phase purification method was disclosed by Heath (U.S. Pat. No. 5,973,137), which used low pH lysing and precipitation reagents. However, liquid phase methods have serious disadvantages in that they involve tedious precipitation steps, and are consequently difficult to automate. Thus, the need for high-throughput RNA purification has led to the development of solid phase methods.

As with liquid phase purification, conventional solid phase methods have been developed to generate highly purified RNA. Generally, these methods require four general steps: lysing cells or viral coats to release RNA; binding the released RNA to a solid support; washing away impurities; and then eluting the purified RNA. The first two steps, lysing the cells or viral coats and binding the released RNA, have traditionally required hazardous reagents.

For solid phase nucleic acid isolation methods, many solid supports have been used including membrane filters, magnetic beads, metal oxides, and latex particles. Probably the most widely used solid supports are silica-based particles (see, e.g., U.S. Pat. No. 5,234,809 (Boom et al.); International Publication No. WO 95/01359 (Colpan et al.); U.S. Pat. No. 5,405,951 (Woodard); International Publication No. WO 95/02049 (Jones); WO 92/07863 (Qiagen GmbH). One method for binding nucleic acids to silica is by the use of chaotropic agents. For example, the method disclosed in U.S. Pat. No. 5,234,809 (Boom et al.) uses a high concentration chaotropic solution such as guanidine isothiocyanate to bind DNA to silica particles and requires six centrifugation steps and five reagents to purify DNA from whole blood.

Polycationic solid supports have also been used in the purification of nucleic acids from solutions containing contaminants. See U.S. Pat. No. 5,599,667 (Arnold et al.). Polycationic supports selectively adsorb nucleotide multimers based on their size, the larger multimers having a higher affinity for the polycationic support than the smaller ones. This method is based largely on the affinity between positively charged cationic solid supports and negatively charged phosphate backbones of nucleotides. Larger nucleotide multimers have higher charges and will consequently bind preferentially over smaller nucleotide multiniers. Thus, the method of Arnold is suited to the isolation of nucleotide multimers based on size rather than the isolation of all types of RNA from crude biological materials. Furthermore, the method of Arnold limits itself to the use of polycationic supports composed of cations such as ammonium, immonium and guanidinium ions.

The use of chaotropic salts for the binding and purification of RNA is well known in the art. In one method, See U.S. Pat. No. 5,990,302 (Kuroita et al.), the biological material is lysed in an acidic solution containing a lithium salt and a chaotropic agent such as guanidinium isothiocyanate (GITC), after which the RNA is brought into contact with a nucleic acid-binding carrier such as silica. The RNA is subsequently purified by eluting it from the silica in a low ionic-strength buffer. This method is disadvantageous in its use of hazardous substances such as the chaotropic salt, guanidine isothiocyanate.

Methods of Inactivating and/or Denaturing Proteins

Several methods are known for inactivating and/or denaturing most enzymes and proteins. As used herein, the term "inactivating" means that an enzyme is rendered unable to carry out the enzymatic reaction, generally due to environmental conditions. Enzymatic inactivation is reversible; i.e., once the conditions are changed, the enzyme will be active again. The term "denaturating" refers to the irreversible modification of a protein or enzyme such that even if the environment returns to a normal or favorable condition, the protein will not re-fold into its normal state at physiological conditions, and/or an enzyme will not be able to carry out its enzymatic reaction. Generally, denaturing is performed such that the structure of the protein or enzyme is modified, and not just the function of the protein or enzyme. Methods of denaturing or inactivating proteins or enzymes include heating, changing pH away from optimum pH, or the presence of organic solvents (such as alcohols), high salt concentration, and/or ionic detergents.

Many researchers use heat to denature proteins or enzymes. Heating steps of 65–70° C. are generally required to denature enzymes. For example, it is recommended by several researchers that heating at about 75° C. for 10–15 minutes is required in order to eliminate DNase I activity. Some protocols teach heating to as much as 90° C. Heat denatures proteins or enzymes by mediating the disruption of the tertiary structure of the molecules. For example, heat may break disulfide bonds and/or hydrogen bonds. Heat treatment, however, also promotes hydrolysis of RNA that may be present in a sample, and promotes subsequent degradation of the RNA. Thus, heat can result in destruction of the nucleic acid that the user is trying to preserve and analyze. Researchers who work with RNA usually attempt to avoid heating their RNA, since RNA has a tendency to degrade, and more quickly as the temperature is increased, either due to residual RNase enzyme activity in the solution or due to the fact that catalytic degradation of the RNA by metal ions also has a tendency to occur much more quickly at higher temperatures.

Another method of protecting RNA from enzymes is to contact the RNA with a salt that precipitates the RNA in the sample along with the cellular protein. This co-precipitation of the RNA and the cellular proteins is believed to render the RNA inaccessible to nucleases via physical means, while the action of the RNA preservation medium simultaneously inactivates or inhibits the action of the nucleases.

A. Protein Denaturing Formulation

The present invention provides reagents, methods, and kits that incorporate a formulation for denaturing proteins or enzymes present in a nucleic acid sample without adversely affecting the nucleic acid. The purified RNA is suitable for use in widely used analytical and diagnostic methods such as RT-PCR and microarray analyses that require substantially pure and undegraded RNA.

The present invention provides a formulation that is used to purify RNA from a variety of biological materials without the use of hazardous substances such as phenol, and chloroform, or hazardous chaotropic substances such as guanidinium salts, urea, etc. The formulations taught by the present invention allow effective denaturation of nucleases without use of hazardous substances.

The formulation taught by the invention includes a unique Protein Denaturing Formulation. This formulation, used in conjunction with an appropriate solid support, may used to generate undegraded RNA, which is substantially pure and contaminant-free.

The Protein Denaturing Formulation of the present invention contains a lithium salt (such as lithium chloride or lithium bromide), an alcohol and citrate. The present solution does not contain hazardous chaotropic substances such as guanidinium salts, urea, etc. The Protein Denaturing Formulation of the present invention is unique in that it requires no added strong chaotropic substances such as guanidinium salts, urea, etc. Further, the method does not require heat to denature the protein.

Guanidinium salts and urea are strong chaotropic salts that disrupt the structure of water and thus tend to decrease the strength of hydrophobic interactions resulting in a drastic effect on other solute molecules. For example, urea, when dissolved in water, disrupts the secondary, tertiary, and quaternary structures of proteins, and subsequently causes dissociation of proteins from RNA. Guanidinium salts and urea dissolve in water through endothermic reactions. Both guanidinium salts and urea are considered to be strongly chaotropic salts as defined by the Hofmeister series, a widely used system that ranks cations and anions according to relative chaotropic strength (F. Hofmeister, *On the understanding of the effects of salts*, Arch. Exp. Pathol. Pharmakol. (Leipzig) 24 (1888) 247–260).

Unlike strong chaotropic salts, the reaction of lithium salts (such as lithium chloride and lithium bromide) in water is an exothermic reaction and is indicative of the tremendous ion-dipole interaction exhibited by the strong kosmotropic lithium ion and the resulting large solubility. Differences such as these are indicative of the differences between the strong chaotropic substances, such as guanidinium salts, and the alkali-metal salts, especially lithium chloride, of the present invention. Lithium salts used to practice the present invention include, but are not limited to, lithium chloride and lithium bromide. Lithium fluoride and lithium iodide are less desirable alkali salts because their cost is about five times the cost of the lithium chloride and bromide salts. In addition, lithium ion is the only clearly kosmotropic ion in the aforementioned list. The sodium ion is a borderline kosmotrope, while potassium, rubidium and cesium ions are chaotropic ions (Collins, K. *Sticky Ions in Biological Systems*, Proc. Natl. Acad. Sci. USA, 92 (1995), 5553–5557). Cesium chloride costs about five times more than the other alkali metal chloride salts and has more limited solubility behavior than the lithium chloride and bromide salts. In addition, sodium, potassium and ammonium chloride salts have much more limited solubility behavior as compared to the lithium chloride and bromide salts, as exhibited by the large exothermic heats of solution exhibited by lithium salts in water (CRC Handbook of Chemistry and Physics, 62nd edition, CRC Press, Boca Raton, Fla.). In one embodiment, the lithium salt is lithium chloride (LiCl). LiCl is very soluble in alcohol-containing solutions. It is much more soluble than most other salts (lithium salts are highly soluble salts and have exothermic heats of solution).

In certain embodiments, the alcohol used in the Protein Denaturing Formulation is either ethanol or methanol. In one embodiment, ethanol was a more effective denaturant.

The present inventors observed that alcohol and high lithium salt as a combination were not sufficient at complete denaturation of DNase enzymes. A third component was the added to the solution. Since DNase I enzyme is stabilized by metal ions, citrate was added to the solution to chelate and remove metal ions from the active site of the DNase I enzyme molecules. This three-component formulation was found to be highly effective in denaturing DNase I.

The challenge at this point was to attain the correct proportions of the three components (alcohol, lithium and citrate), such that the citrate did not precipitate out the alcohol/high lithium solution, since the alcohol was almost saturated with lithium salt. It was found that the Protein Denaturing Formulation should have the following concentrations: (1) alcohol, about 25–40% v/v (such as about 28–35% ethanol, or about 30% ethanol), (2) lithium salt, about 2.5–4.0 M (such as about 3.2–3.8 M LiCl, or about 3.5 M LiCl), and (3) citrate, about 25–100 mM (such as about 40–75 mM trisodium citrate, or about 50 mM trisodium citrate). It should be noted that the Protein Denaturing Formulation excludes the use of EDTA. It was found that EDTA tends to precipitate out of solution, because of the high salt concentration. It was not possible to have an effective concentration of EDTA, and have it remain in solution. Further, EDTA inactivates DNase enzymes, but does not denature DNase enzymes. The presence of the citrate buffers the Protein Denaturing Formulation, such that the Formulation maintains a pH of about 7. It was surprising that the Protein Denaturing Formulation so effectively denatured. DNase I at neutral pH, considering optimal working pH for DNase I is about 7.5–8.0. Thus, the Protein Denaturing Formulation must even more rigorously denature the enzymes since the pH does not assist in inactivating the enzymes.

B. Solid Supports

A variety of solid supports may be used in the present invention. These include silica-based solid supports and solid supports made of cellulose, cellulose acetate, nitrocellulose, nylon, polyester, polyethersulfone, polyolefin, polyvinylidene fluoride, and combinations thereof. The size of the solid support suitable for use with the reagents of this invention may vary according to the volume of biological material. For example, glass fiber membranes may be cut to different sizes, in order to allow for the binding, purification and elution of different quantities of RNA.

In one embodiment, the solid support may be a material that permits the preferential binding of nucleic acids to the solid support instead of other biological contaminants in the presence of the Protein Denaturing Formulation described above. Such a solid support may be a silica-based or borosilicate glass fiber material. Glass fiber materials provide a better yield because of the specific binding properties to the electropositive silicon and boron atoms, and because of hydrogen bonding properties of the silicate surface.

Because of the specificity of silica for nucleic acids, more RNA is bound relative to other contaminants and the eluted product is made more substantially pure.

The shape of the solid support suitable for use with the reagents of this invention may be, for example, a sheet, a precut disk, cylinder, single fiber, or a solid support composed of particulates. The material of the solid support may be packed so as to create a free-standing solid support such as a membrane, disk, or cylinder that may be immobilized or encased in a suitable vessel. If necessary, the solid support is contained in an appropriate vessel, e.g., a paper form (such as a Guthrie card), a microcentrifuge tube, a spin tube, a 96-well plate, a chamber, or a cartridge. If the solid support comprises fibers, it may be encased in a suitable vessel so as to pack the fibers appropriately, allow for optimal nucleic acid binding, and the washing away of contaminants such as protein, phospholipids, etc.

In order that the invention may be better understood, specific embodiments for vessels that contain the solid support will now be described in more detail.

In one embodiment of this invention, the vessel is a cartridge equipped with one or more inlet ports or pierceable septa at the top. The inlet ports are attached to vessels upstream containing the sample or reagents through a connector, such as a female Luer-Lock. One inlet, the sample port, is used for the application of the biological sample to the solid support. An optional feature on the sample port is a self-sealing mechanism that seals the sample port after sample has been transferred through it. The second inlet serves as a reagent port. An optional feature on both inlet ports is a protective breakaway seal. Furthermore, the inlet ports, breakaway seals and diffuser may be housed in an optional screw-cap. At the bottom of the solid support is an optional diffuser with a pore size suitable for the dispersion and passage of cellular debris, proteins and lipid molecules. The diffusers allow for a uniform traversal of biological material across the cross section of the cartridge, and prevent unequal buildup of biological material anywhere above or below the solid support. The outlet of the cartridge comes equipped with a protective cap that fits neatly over the tapered barrel. The purified RNA is collected in a collection tube that consists of a conical tube with a snap cap for easy and contamination-free storage. The entire vessel can be scaled in size depending on the size of the samples to be processed and the yields needed for subsequent analysis.

In another embodiment of this invention, the vessel is a spin tube designed to hold an insert into which the solid support is packed. The solid support may be silica-based, cellulose, cellulose acetate, nitrocellulose, nylon, polyester, polyethersulfone, polyolefin, polyvinylidene fluoride, and combinations thereof In one embodiment, the support is a silica-based borosilicate glass fiber membrane. The insert has a flanged top to hold it in the spin tube and a perforated bottom to allow fluids to pass through while supporting the solid support. A cap tethered to the spin tube may be used to cover the insert. Solutions, for instance, Protein Denaturing Formulation, pass through the perforated bottom and are collected at the bottom of the spin tube by centrifugal forces that draw out the solutions.

In yet another embodiment, the vessel may be multiple well plates, for example, 6, 12, 24, 48, 96, or 384 well plates where a solid support is packed into each well. The bottom of each well has an exit port through which solutions containing contaminants or purified RNA can pass.

The unique combination of the solid support of choice with the unique reagent—Protein Denaturing Formulation—results in the isolation of substantially pure, undegraded RNA.

C. Methods of the Present Invention

The present invention also teaches methods for denaturing proteins, enzymes in particular, which may be present in a sample containing a nucleic acid, such as RNA. The Protein Denaturing Formulation is simple, efficient, and versatile. The Protein Denaturing Formulation may be added directly to a sample containing a nucleic acid in order to inactivate and/or denature any proteins present. Alternatively, the Protein Denaturing Formulation may be used to wash a solid support in order to inactivate and/or denature any proteins that might be present on the solid support. Suitable solid supports include silica-based supports such as glass fiber, or other materials such as cellulose, cellulose acetate, nitrocellulose, nylon, polyester, polyethersulfone, polyolefin, polyvinylidene fluoride, and combinations thereof. The solid support may be encased or immobilized in a vessel to enable plug-flow or continuous-flow RNA isolation methods. Alternately, the material of the solid support may be packed so as to create a free-standing solid support such as a membrane, disk, or cylinder that may be immobilized or encased in a suitable vessel, such as a tube or plate. In one embodiment, the solid support may be fibrous or particulate to allow optimal contact with the biological material.

The present invention also provides kits for denaturing proteins, enzymes in particular, which may be present in a sample containing a nucleic acid. The kit contains instruction means for denaturing proteins that may be present in a sample, and Protein Denaturing Formulation, either as a separate solution or pretreated onto a solid support. In addition, the kit can include auxiliary components such as a proteinase K solution and a pre-clear column for use with tissue samples, a vessel to contain the solid support, vessels to contain substantially pure and undegraded RNA, and combinations thereof. Substantially pure, undegraded RNA is RNA that is suitable for use in subsequent analyses known to those with skill in the art, for example, RT-PCR, in vitro translation, northern blotting, microarray analysis etc.

The present invention provides reagents, methods and kits for denaturing proteins that may be present in a sample containing a nucleic acid. The nucleic acid may be RNA. The methods and kits of the present invention isolate a wide range of RNAs. Candidate RNAs include, but are not limited to, ribosomal RNA, messenger RNA, transfer RNA, and viral RNA, or combinations thereof, all of which can be recovered over a wide molecular weight range.

The reagents, methods and kits of the present invention provide substantially pure and undegraded RNA such that the RNA may be used in downstream processes such as RT-PCR and microarray analyses. As used herein, "substantially pure" means substantially free of protein (e.g., enzymes), such that the RNA can be used in subsequent analyses known to those with skill in the art such as RT-PCR and microarray analyses. As used herein, "substantially undegraded" RNA means nondigested or intact RNA, which can be readily determined by one of skill in the art using standard techniques. That is, the RNA is not damaged by enzymatic, physical or chemical means during the purification methods of the present invention.

The substantially pure and undegraded RNA obtained from practicing the invention can also be evaluated for purity, yield, size, reverse transcriptase or other hybridization processes, amplification, hybridization ability, etc. The substantially pure and undegraded RNA is representative of the total RNA found in the biological sample, and is typically a combination of, but not restricted to, mRNA, tRNA, rRNA, and viral RNA.

All of the raw materials mentioned below are readily available from commercial sources such as Sigma Chemical Company, St. Louis, Mo. All percentages are in volume per volume, based on the total volume of the reagent, unless specified otherwise.

EXAMPLE 1

Cost Analysis

In order to produce the best quality Protein Denaturating Formulation product, the product must function exceptionally well in several respects. The product must effectively denature protein that might be present in a sample that contains a nucleic acid. It must be user-friendly, meaning the steps must not be too onerous, and the components must not be toxic and can be disposed of easily. Further, the product must be economical for the user. Therefore, finding cost effective components for the solutions was essential. Table 1 shows the cost for each of the salts evaluated herein.

TABLE 1

| Salt | Cost | |
|---|---|---|
| | Amount (grams) | Cost ($) |
| $BeCl_2$ | 25 | 600.00 |
| $CaCl_2$ | 500 | 105.00 |
| CsCl | 500 | 340.00 |
| KCl | 500 | 30.00 |
| LiBr | 500 | 65.00 |
| LiCl | 500 | 60.00 |
| LiF | 50 | 400.00 |
| LiI | 250 | 330.00 |
| $MgCl_2$ | 500 | 50.00 |
| NaCl | 500 | 24.00 |
| $NH_4Cl$ | 500 | 22.00 |

Although the lithium salts work well for the methods of the present invention, the lithium salts LiF and LiI are expensive, and additionally, LiF is quite hazardous. LiCl works very well with the methods of the present invention and costs about $60–65 per 500 grams.

EXAMPLE 2

Treatment of a Glass Fiber Column with Protein Denaturation Formulation

Prior to using DNase for the first time, 2.5 ml of DNase Buffer (Gentra Systems, Inc.) was added to the lyophilized DNase Enzyme (1300 Units). The tube was inverted gently to mix. The tube containing the enzyme in buffer may be stored on ice during use. Following the first use of DNase, the DNase is aliquoted into appropriate volumes for subsequent RNA isolations and stored frozen at −20° C. or −80° C. Enzyme in buffer solution may be subjected to three freeze/thaw cycles and still retain sufficient DNase activity.

In this example, a sample was homogenized, the cells were lysed, and Wash I Solution (Gentra Systems, Inc.) was added as outlined in the manufacturer's RNA purification protocol. 50 μl DNase was applied to the column. The column was incubated at room temperature for 15 minutes in order to eliminate the presence of any DNA. Next, 200 μl of Protein Denaturation Formulation (DNase Wash Solution, Gentra Systems Inc.) was added-to the column to denature the DNase I enzyme present in the glass fiber column. The column was centrifuged at 13,000–16,000×g for two minutes in order to denature and wash away the DNase I enzyme. The column was transferred to a new 2.0 ml tube (provided in the DNase Kit, Gentra Systems Inc.). Wash 2 Solution (Gentra Systems Inc.) was then added according to manufacturer's RNA purification protocol.

The results indicated that the DNase was denatured.

EXAMPLE 3

Determination of Elimination of Enzyme Activity

Nucleic acid contacted with the Protein Denaturation Formulation was tested in a PUC 19 Assay. This assay determines whether supercoiled (double-stranded) DNA is nicked to form circular PUC, as observed on an agarose gel. The results indicated that the DNA was not nicked, showing that the Protein Denaturation Formulation effectively denatured any DNase I that was present in the original sample.

Nucleic acid was also subjected to RT-PCR. Even though the primary substrate for DNase I is double stranded DNA, the enzyme can pose a threat to reverse transcription because it does have some limited activity on RNA-DNA hybrids and single stranded DNA (cDNA). The RNA that had been treated with the Protein Denaturation Formulation provided an effective template for RT-PCR.

All publications, patents and patent documents are incorporated by reference herein, as though individually incorporated by reference. The invention has been described with reference to various specific and specific embodiments and techniques. However, it should be understood that many variations and modifications can be made while remaining within the scope of the invention.

I claim:

1. A formulation for denaturing proteins comprising:
a lithium salt at a concentration of about 2.5–4.0 M,
an alcohol at a concentration of about 25–40% v/v, and
a citrate at a concentration of about 25–100 mM.

2. The formulation of claim 1, which formulation lacks EDTA.

3. The formulation of claim 1, wherein the formulation lacks a chaotropic substance.

4. The method of claim 3, wherein the chaotropic substance is guanidinium salt, urea, ammonium, cesium, rubidium, potassium, or iodide salt.

5. The formulation of claim 1, wherein the lithium salt is lithium chloride or lithium bromide.

6. The formulation of claim 1, wherein the lithium salt is lithium chloride.

7. The formulation of claim 1, wherein the lithium salt is at a concentration of about 3.5 M.

8. The formulation of claim 1, wherein the alcohol is ethanol or methanol.

9. The formulation of claim 1, wherein the alcohol is ethanol.

10. The formulation of claim 1, wherein the alcohol is at a concentration of about 30% alcohol.

11. The formulation of claim 1, wherein the citrate is trisodium citrate.

12. The formulation of claim 1, wherein the citrate is at a concentration of about 50 mM.

13. The formulation of claim 1, wherein the formulation has a pH between about 6 and about 8.

14. The formulation of claim 1, wherein the solution has a pH between about 7.0 and about 7.5.

15. A method for denaturing protein from a solid support, comprising contacting the solid support with the formulation of claim 1, such that protein present on the solid support is denatured.

16. The method of claim 15, wherein the protein is an enzyme.

17. The method of claim 16, wherein the enzyme is a DNase.

18. The method of claim 17, wherein the DNase is DNase I.

19. The method of claim 15, wherein the solid support comprises components of silica, cellulose, cellulose acetate, nitrocellulose, nylon, polyester, polyethersulfone, polyolefin, or polyvinylidene fluoride, or combinations thereof.

20. The method of claim 15, wherein the solid support is contained in a vessel, wherein the vessel is a centrifuge tube, spin tube, syringes, cartridge, chamber, multiple-well plate, or test tube, or combinations thereof.

21. A method for purifying substantially pure and undegraded RNA from biological material comprising RNA, comprising the steps of:

(a) contacting a solid support with the formulation of claim 1, such that protein present on the solid support is denatured;

(b) contacting the solid support with a sample comprising RNA such that the RNA binds to the solid support;

(c) washing the solid support with a series of wash solutions to remove biological materials other than bound RNA, wherein the series of wash solutions comprises a first wash containing alcohol and an RNA-complexing salt at a concentration of at least 1M and a second wash containing an alcohol, buffer and an optional chelator; and (d) preferentially eluting the bound RNA from the solid support with an RNA elution solution in order to obtain substantially pure RNA.

22. The method of claim 21, wherein the solid support is contained in a vessel, wherein the vessel is a centrifuge tube, spin tube, syringe, cartridge, chamber, multiple-well plate, test tube, or combination thereof.

23. The method of claim 21, wherein the RNA-complexing salt is lithium chloride.

* * * * *